United States Patent
Hamedat-Schumacher et al.

[11] Patent Number: 5,962,847
[45] Date of Patent: Oct. 5, 1999

[54] CYLINDRICAL DEVICE FOR OPTICAL QUALITY CONTROL OF A STRIP-LIKE MATERIAL

[76] Inventors: Ursula Hamedat-Schumacher, AM Tivoli 24; Thomas Ischdonat, Urgarnstr. 18, both of D-52070 Aachen; Heinz-Wilhelm Dederichs, Schweilbacherstr. 30, D-52146 Würselen, all of Germany

[21] Appl. No.: 08/952,129
[22] PCT Filed: May 1, 1996
[86] PCT No.: PCT/DE96/00752
 § 371 Date: Jan. 28, 1998
 § 102(e) Date: Jan. 28, 1998
[87] PCT Pub. No.: WO96/35113
 PCT Pub. Date: Nov. 7, 1996

[30] Foreign Application Priority Data
May 2, 1995 [DE] Germany .......................... 195 15 373

[51] Int. Cl.⁶ ..................................... H01J 5/16
[52] U.S. Cl. ......................................... 250/227.11; 250/221
[58] Field of Search ............................ 250/227.11, 221, 250/239, 228, 227.14, 227.22, 227.24; 356/432, 426

[56] References Cited

U.S. PATENT DOCUMENTS 4,972,074 11/1990 Wright ............................... 250/227.11

Primary Examiner—Que T. Le
Attorney, Agent, or Firm—John Lezdey & Assoc

[57] ABSTRACT

The invention is for a device for sensing radiation directed from a radiation source on a travelling strip-like sample and radiation reflected from or transmitted through the sample with a rotary cylindrical roller having at least one radiation-transparent sensing point at the periphery of the roller, a central radiation-transparent decoupling point at one end and a central radiation-transparent point at the other end. Inside the roller, there are light guides to guide the radiation from the coupling point to the sensing point(s) and from there to the decoupling point.

14 Claims, 1 Drawing Sheet

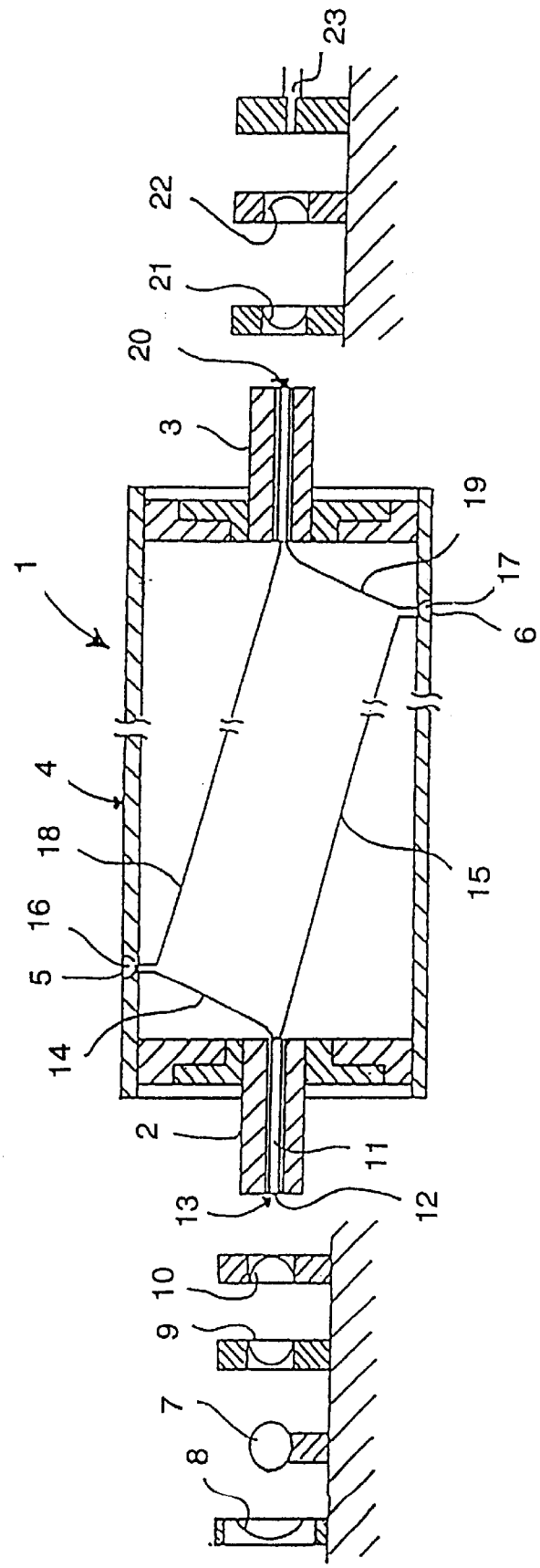
The Figure

CYLINDRICAL DEVICE FOR OPTICAL QUALITY CONTROL OF A STRIP-LIKE MATERIAL

BACKGROUND OF THE INVENTION

1. Field of the Invention

The invention relates to a device for sensing radiation from a radiation source on a traveling strip-like sample reflected from or transmitted through the sample.

With certain kinds of products, it seems sensible or even necessary, to perform quality controls during the production, for example with regard to the material composition of the product. Such controls are often performed by means of the interaction of radiation, for example infra red radiation, with the samples to be tested. Thereby the sample is exposed to the radiation and the radiation, transmitted through the sample or reflected from the surface of the sample, is guided to a unit of analysis. Thereby it is desired that, the measures for the quality control are integrated into the production process in such a way that this process is disturbed as little as possible.

2. Description of the Prior Art

In the case of traveling strip-like products, as for example paper and textile webs, it is known to admit a radiation to the traveling product at a certain position of the path of the product and to capture a largest possible fracture of the reflected or transmitted radiation with radiation absorption devices, which in a fixed position. To make sure that as little as possible of this radiation is lost, it is favorable to guide these radiation absorption devices as close to the sample to be tested as possible. If the radiation absorption devices are mounted onto the traveling sample directly, it leads to the disadvantage of an effect of the friction, which may impair the product.

SUMMARY OF THE INVENTION

It is the task of the present invention to provide a device of the above mentioned kind which guarantees a high effect of the radiation to be analyzed and which avoids a mechanical damage of the sample to be tested.

With a device of the above mentioned kind this task is solved by a rotary cylindrical roller, whose periphery contacts the strip-like sample with power conformity and which has at least one radiation transparent sensing point at the periphery and a central radiation-transparent decoupling point at one end, and by means positioned inside the roller for the transmission of the radiation from the sensing point(s) to the decoupling point.

Such a roller can be put into the path of the production of a traveling strip-like sample without disturbing the production process. When the strip-like sample is guided via the roller, the radiation absorption devices, sensing the radiation to be analyzed, contact the surface of the sample. That way the entire radiation, deriving from the part covered by the sensing point of the surface of the sample, is captured by the sensing points.

In the running operation of the production the speed of the surface of the roller corresponds to the speed of the traveling sample, so that there is no sliding friction between the two surfaces. If the radiation is sent to the side of the strip-like sample, which is opposite of the periphery of the roller, then the radiation transmitted by the sample is analyzed.

The device according to the invention can also be embodied in such a way that positioned at the other end of the roller it provides a central radiation-transparent coupling point, deriving directly from the radiation source, and that is has means for the transmission of the radiation which is directed in via the coupling point, to each sensing point.

Hereby the radiation, deriving from the radiation source is sent to the surface of the sample to be analyzed via the inside of the roller and the light reflected therefrom is guided back out of the roller to the analysis.

The device according to the invention can also be embodied in such a way that at least two of the sensing points on the roller have different angles of the periphery with regard to the cylinder system of coordinates.

That way it is guaranteed, that if the roller turns one single time, several consecutive points, positioned in the direction of the movement of the sample, of the surface of the sample can be examined.

Furthermore the device according to the invention can be embodied in such a way that at least two of the sensing points on the roller have different heights with regard to the cylinder system of coordinates.

That way measurements via the width of the strip-like sample can be performed.

The device according to the invention can also preferably be embodied in such a way that it has means for recording and controlling an absolute position of the angle of the roller.

If the absolute position of the angle of the roller is known, then it is known at the same time which of the sensing points is in contact with the strip-like sample at this point in time.

The device according to the invention can also be embodied in such a way that it has at least one fixed induction sensor, which is positioned in a certain radial distance of the axis of rotation and that it has a position element, turning with the roller, having an effect on the induction sensor.

Furthermore the device according to the invention can be embodied in such a way that the position element is a disk with at least one opening, running directly along the induction sensor when turned.

An advantageous embodiment of the device according to the invention is achieved by a first and a second induction sensor, whereby the induction sensors have different radial distances from the rotation axis of the roller, and by a position disk, which has at least one perforation on the position of the radius corresponding to the first induction sensor and at least two perforations on the radius corresponding to the position of the second induction sensor.

The induction sensor registering the individual perforation sends a signal, when the roller has performed a complete turn. That way the position of the roller can be calibrated with every complete turn.

An advantageous embodiment of the device according to the invention can also be achieved by the fact that inside the roller, light guides are provided for the transmission of the radiation.

That way the formation of the guidance of the path of the rays is especially simple, as the adjustment of alternative optic elements, as for example lenses and mirrors, can be avoided.

Furthermore it is advantageous, to embody the device according to the invention in such a way that the radiation, deriving directly from the radiation source, is coupled in a bundle of input fibers via the coupling point and the same number of fibers is guided to each sensing point.

If the coupling point is evenly illuminated by the radiation source, the parts of the surface of the sample, which are positioned above the different sensing points, are impinged with about the same intensity of radiation.

Furthermore the device according to the invention can be embodied in such a way that starting from each sensing point, the same number of decoupling fibers are guided into a bundle, leading to the decoupling point.

That way, all sensing points are optically connected with the decoupling point. As it is generally not possible to perform a separation according to the decoupling fibers, deriving from the various sensing points, within the bundle, it seems sensible to chose the belt wrap of the strip-like sample on the roller in such a way that only one sensing point is in contact with the surface of the sample at all times. If the absolute position of the angle of rotation of the roller is known, then it is also known which of the sensing points is in contact with the surface of the sample.

An advantageous embodiment of the device according to the invention can also be achieved by a cut surface at the periphery of the roller.

The cut surface of the roller guarantees that the sensing points on the surface of the roller do not cause any unevenness.

Furthermore the device according to the invention can be embodied in such a way that the roller consists of a carbon fiber intensified synthetic material.

The carbon fiber intensified synthetic material has the advantage of a low density, whereby as against alternative material as for example special steel, the weight of the roller is reduced. Furthermore the coefficient of expansion of the carbon fiber intensified synthetic material is close to zero, that is why the geometrical sizes of the roller do not change drastically at temperature changes due to the production process.

Finally the device according to the invention can be embodied in such a way that it has a pushing roller, which presses the strip-like sample onto the roller.

That way a constant and good contact is guaranteed constantly between the surface of the sample and the surface of the roller.

BRIEF DESCRIPTION OF THE PREFERRED DRAWINGS

In the following an embodiment of the device according to the invention is illustrated by a representation.

It is illustrated in

DESCRIPTION OF THE PREFERRED EMBODIMENTS

The Figure a schematic illustration of a cross-section through an embodiment of the device according to the invention.

A roller 1 is movably positioned by means of two pinions 2 and 3 in a mounting, which is not illustrated here. In its use per definition, the roller is integrated in a rotating way into the production path of a traveling strip-like sample, which is not illustrated here, that the strip-like sample runs across the periphery of the roller 1. Driven by the strip-like sample itself, the periphery 4 of the roller 1 gains the same speed as the strip-like sample, so that between the two kinds of materials no sliding processes occur.

Three sensing points are integrated into the periphery 4 of the roller 1, of which only two sensing points 5 and 6 are illustrated in the example. These sensing points 5, 6 make it possible, for example with the help of infrared radiation, to test the surface of the strip-like sample with regard to certain characteristics. Hereby the surface of the sample needs to be impinged with a radiation. This is achieved in such a way that the radiation, deriving from a source of radiation 7, is focused onto optical fiber beams 11, with optical instruments such as a mirror 8 and optical lenses 9 and 10. The final coupling point 12 of the optical fiber beams 11 is positioned at the coupling point 13 at the end of the pinion 2. The optical fiber beams 11, which consist of a multitude of input fibers, are guided through the pinion 2 into the inside of the roller. Parts of the beams 14 and 15 from the optical fiber beams 11 are guided to the sensing points 5 and 6 inside the roller 1, whereby each sensing point 5 and 6 is allocated to the more or less same amount of input fibers, so that both sensing points 5 and 6 are impinged with the same intensity of radiation. At the sensing points 5 and 6, hemispherical glass objects 15 and 16 are integrated in the periphery 4 of the roller 1, which are coupled with the parts of the beams 15 and 16 in an optical manner. These glass objects 15 and 16 are cut together with the periphery 4 of the roller 1, so that there is no unevenness on the surface of the roller in the area of the sensing points 5 and 6.

The radiation guided via the parts of the beams 14 and 15 is led via the glass objects 16 and 17 onto the surface of the strip-like sample, when the respective sensing point 5 or 6 is just positioned in the area, wrapped by the strip-like sample, of the roller 1. The radiation, led to the surface of the strip-like sample via the sensing points 5 or 6, interacts with this surface and is then reflected into the glass object 16 or 17 again. Besides the part of the beams 14 or 15 of the input fibers, a further part of the beams 18 or 19 of the decoupling fibers is optically coupled at each glass object 16 and 17. A part of the radiation, which is reflected from the surface of the strip-like sample, reaches the part of the beams 18 or 19 of the decoupling fibers and is guided through the pinion 3 to the decoupling point 20 at the end of the pinion 3. The radiation emitting at the decoupling point 20 is coupled via the lenses 21 and 22 in a further light guide 23, which guides the radiation to a unit of evaluation, which is not illustrated here.

The belt wrap of the strip-like sample on the roller 1 and the distribution of the sensing points 5, 6 are coordinated in such a way that only one of the sensing points 5, 6 is always in contact with the strip-like sample. By a measuring system, which is not illustrated here, for the determination of an absolute position of the angle of rotation of the roller 1 it is possible to detect which of the sensing points 5 or 6 is just in the wrap area. That way the radiation, registered at the decoupling point 20 can be definitely allocated to a certain position of the surface of the sample.

The sensing points 5, 6 are arranged on the periphery 4 of the roller 1 on a spiral line in such a way that the sensing points are distributed evenly along the length of the roller 1, seen in the direction of its angle of rotation, and that sensing points, positioned in a sequence on the spiral line, are always separated from each other by the same angle at circumference. With this arrangement of the sensing points 5, 6, measuring profiles can be detected either via the length or via the width of the strip-like sample.

List of reference points:
1. roller
2. pinion
3. pinion
4. periphery
5. sensing point
6. sensing point
7. radiation source
8. mirror
9. lens 10. lens
11. optical fiber beams
12. final coupling point
13. coupling point
14. part of the beams
15. part of the beams
16. glass object
18. part of the beams
19. part of the beams
20. decoupling point
21. lens
22. lens
23. light guide

What is claimed is:

1. A device for sensing radiation directed from a radiation source onto a moving strip-like sample and for sensing radiation reflected from or transmitted through the said sample comprising:

a rotary cylindrical roller having an end portion, an inside portion and a periphery;

said periphery contacting said strip-like sample in a manner whereby movement of the said strip-like sample causes corresponding rotation of the said rotary roller;

said periphery having at least one radiation-transparent sensing point located thereon;

said end portion having at least one central radiation-transparent decoupling point; and a means located in said inside portion of the roller for the transmission of radiation from said sensing point to said decoupling point.

2. The device according to claim 1 further comprising:

a central radiation-transparent coupling point directly directed from the said radiation source; said coupling point located at the end of said roller opposite said decoupling point; and means for the transmission of the radiation, directed from said coupling point to each said sensing point.

3. The device according to claim 1 wherein at least two of said sensing points on said roller have different angles at circumference with regard to a cylinder system of coordinates.

4. The device according to claim 1 wherein at least two of said sensing points on said roller have different heights with regard to a cylinder system of coordinates.

5. The device according to claim 1 further comprising means for the recording and controlling of an absolute position of the angle of rotation of said roller.

6. The device according to claim 5 further comprising at least one fixed induction sensor, said induction sensor being positioned in a certain radial distance of the angle of rotation of said roller; and having a position element, said position element turning with said roller and having an effect on the induction sensor.

7. The device according to claim 6 wherein the position element is a disk with at least an opening, said disk running directly along said induction sensor when turned.

8. The device according to claim 7 further comprising a first and a second induction sensor, whereby said induction sensors have different radial distances from the axis of rotation of said roller, and having a position disk, said position disk having a perforation on the radius corresponding to the position of the first said induction sensor, and having at least two perforations on the radius corresponding to the position of the second induction sensor.

9. The device according to claim 1 wherein there are light guides inside said roller for the transmission of the radiation.

10. The device according to claim 2 further comprising a bundle of input fibers wherein the radiation, directed directly from the said radiation source is coupled by said coupling point in said bundle of input fibers and wherein to each said sensing point the same number of fibers is guided.

11. The device according to claim 10 further comprising decoupling fibers and a decoupling point wherein from each sensing point the same number of said decoupling fibers is guided into said bundle leading to said decoupling point.

12. The device according to claim 1 having a cut surface at the periphery of said roller.

13. The device according to claim 1 wherein said roller consists of a carbon fiber intensified synthetic material.

14. The device according to claim 1 further comprising a pushing roller, said pushing roller pressing the strip-like sample onto said roller.

* * * * *